(12) United States Patent  
Saito (10) Patent No.: US 7,871,461 B2
(45) Date of Patent: Jan. 18, 2011

(54) BUBBLE SEPARATOR

(75) Inventor: Yasuhiro Saito, Aichi-ken (JP)

(73) Assignee: Toyota Boshoku Kabushiki Kaisha, Kariya-Shi, Aichi-Ken (JP)

( * ) Notice: Subject to any disclaimer, the term of this patent is extended or adjusted under 35 U.S.C. 154(b) by 510 days.

(21) Appl. No.: 11/962,502

(22) Filed: Dec. 21, 2007

(65) Prior Publication Data

US 2008/0179227 A1 Jul. 31, 2008

(30) Foreign Application Priority Data

Jan. 25, 2007 (JP) ............................. 2007-015552

(51) Int. Cl.
*B01D 19/00* (2006.01)
(52) U.S. Cl. .............................. 96/174; 96/207; 96/212
(58) Field of Classification Search .................. 96/207, 96/209, 210, 211, 212, 174; 95/261
See application file for complete search history.

(56) References Cited

U.S. PATENT DOCUMENTS

| 2,034,914 A * | 3/1936 | Lanser ......................... 96/174 |
| 5,000,766 A * | 3/1991 | Yano et al. .................... 96/196 |
| 5,510,019 A | 4/1996 | Yabumoto et al. |
| 7,288,138 B2 * | 10/2007 | Showalter et al. ................. 96/1 |
| 7,288,139 B1 * | 10/2007 | Showalter ........................ 96/1 |

FOREIGN PATENT DOCUMENTS

| JP | 5-296018 | 11/1993 |
| JP | 7-039702 | 2/1995 |

OTHER PUBLICATIONS

English language Abstract of JP 5-296018.
English language Abstract of JP 7-039702.

* cited by examiner

*Primary Examiner*—Duane Smith
*Assistant Examiner*—Douglas J Theisen
(74) *Attorney, Agent, or Firm*—Greenblum & Bernstein, P.L.C.

(57) ABSTRACT

A bubble separator capable of performing efficient bubble separation with a compact and simple structure is provided. The bubble separator includes a centrifugal bubble separating mechanism and an auxiliary bubble separating mechanism. The centrifugal bubble separating mechanism has a first bubble separator body in which a first fluid introducing part, a first fluid discharging part, and a first gas discharging part are provided. The auxiliary bubble separating mechanism has a guiding portion, a second bubble separator body, a second fluid introducing part, a second fluid discharging part, and a second gas discharging part. According to the bubble separator of the present invention, in addition to minuscule bubbles it is also possible to separate large bubbles that could not be completely separated using the centrifugal bubble separating mechanism.

16 Claims, 9 Drawing Sheets

BUBBLE SEPARATOR

BACKGROUND OF THE INVENTION

1. Field of the Invention

The present invention relates to a bubble separator. More specifically, the present invention relates to a bubble separator with a compact and simple structure, which is capable of improving a bubble separation efficiency even when there are bubbles of various sizes contained in a fluid. The bubble separator according to the present invention is used in a lubrication system of an internal combustion engine, and is also applicable to food, paint, and other fields.

2. Description of the Related Art

Dry sump and wet sump systems are commonly known as modes for lubricating internal combustion engines. The dry sump system is a type in which engine oil collects in an oil tank and the engine oil is sent under pressure from the oil tank through a feed pump to lubricate respective parts of the engine. Oil that falls into an oil pan is then returned to the oil tank through a scavenge pump. The wet sump system is a type in which engine oil is intaken from the oil pan by a pump and sent under pressure to lubricate respective parts of the engine. Oil that has finished lubricating then falls of its own accord into the oil pan of the engine.

However, in the dry sump system a considerable amount of air bubbles are mixed into the oil while it is being returned to the oil tank via the scavenge pump. The bubbles contained in the oil are subsequently separated by an oil filter or the like, but there is a risk of poor lubrication due to incomplete separation.

On the other hand, in the wet sump system only a relatively small amount of air bubbles are mixed into the oil, and some bubbles are further eliminated by the pressure of the pump. As a consequence, there is little risk of poor lubrication. However, there have been calls to reduce the size of the pump in order to improve fuel consumption performance. In such case, there is a risk that poor lubrication may occur because air bubbles have not been sufficiently eliminated.

Thus, the bubble fraction of oil must be decreased regardless of whether the lubrication system of the internal combustion engine is a dry sump system or wet sump system.

Hence, to solve the above problems a centrifugal separation type of bubble separator has been proposed for removing bubbles contained in the oil (see Patent Documents 1 and 2 for examples).

Patent Document 1 discloses a centrifugal separator type of bubble removing device formed from a swirl chamber of a predetermined shape and a bubble removing pipe that runs through an end of the swirl chamber along a central axis of the swirl chamber.

Patent Document 2 discloses that a ring-like preliminary spiral flow path is formed on an outer peripheral side of an upper end of a cone-shaped container. Within this preliminary spiral flow path, oil swirls around an axial center of the container so as to join minuscule air bubbles contained in the oil, after which the swirl is introduced into the container where centrifugal separation is performed.

However, in the above Patent Documents 1 and 2, the ratio of bubbles and fluid introduced into the bubble separator may differ depending on the pump discharge flow and amount of flow into the upper oil pan. If the bubbles are many or large, gas is carried towards the fluid discharge holes. But if there is little gas, then the fluid is blown away from the gas discharge holes. In other words, many or large bubbles makes full separation of the bubbles and the fluid difficult as some bubbles are discharged together with the fluid. As a consequence, efficient bubble separation cannot be achieved.

Patent Document 1: Japanese Patent Application Publication No. JP-A-H05-296018

Patent Document 2: Japanese Patent Application Publication No. JP-A-H07-39702

SUMMARY OF THE INVENTION

[Problems to be Solved by the Invention]

The present invention was devised in light of the foregoing circumstances, and it is an object of the present invention to provide a bubble separator with a compact and simple structure, which is capable of efficiently performing bubble separation even when there are many or large bubbles in a fluid and also when there are bubbles of various sizes contained in a fluid. More specifically, it is an object of the present invention to provide a bubble separator with a compact and simple structure, which is capable of separating large bubbles as well as small bubbles and consequently achieves efficient bubble separation.

[Means for Solving Problem]

Accordingly, the present invention overcomes the drawbacks of existing bubble separators. In a non-limiting example, the present invention generally provides a bubble separator for removing bubbles included in a fluid, including a centrifugal bubble separating mechanism and an auxiliary bubble separating mechanism at a downstream side and an upstream side of the centrifugal bubble separating mechanism. The centrifugal bubble separating mechanism includes a first bubble separator body, a first fluid introducing part that is provided in the first bubble separator body, and introduces fluid mixed with bubbles inside the first bubble separator body in the tangential direction. A first fluid discharging part is provided in the first bubble separator body, and discharges fluid separated by swirling. A first gas discharging part is provided in the first bubble separator body, and discharges bubbles separated by swirling. The auxiliary bubble separating mechanism includes a second bubble separator body that is provided adjacent to the first bubble separator body, and has a guiding portion for changing the flow direction of introduced fluid. A second fluid introducing part is provided in the second bubble separator body, and introduces the fluid. A second fluid discharging part is provided in the second bubble separator body, and discharges separated fluid. A second gas discharging part is provided in the second bubble separator body, and discharges separated bubbles.

In another embodiment, the auxiliary bubble separating mechanism is provided on a downstream side of the centrifugal bubble separating mechanism, the second bubble separator body has a guiding portion for changing a flow direction of the fluid that was subjected to primary separation and discharged from the first fluid discharging part of the centrifugal bubble separating mechanism while still including residual bubbles, and the second fluid introducing part introduces the fluid that was subjected to primary separation.

In a further embodiment, the auxiliary bubble separating mechanism is provided on an upstream side of the centrifugal bubble separating mechanism, and the fluid that was subjected to primary separation by the auxiliary bubble separating mechanism and discharged from the second fluid discharging part is introduced to the first fluid introducing part.

In yet another embodiment, the guiding portion is a partition formed from a board-shaped body.

In still another embodiment, the second gas discharging part in the auxiliary, bubble separating mechanism has an opening and closing valve that opens and closes depending on a pressure within the second bubble separator body.

In still a further embodiment, the auxiliary bubble separating mechanism is a bent body provided with the second gas discharging part on an upper wall face thereof.

In another embodiment, the first fluid discharging part in the centrifugal bubble separating mechanism has a flow control valve that controls the flow discharged from the first fluid discharging part.

[Effect of the Invention]

According to the bubble separator of the present invention, a centrifugal bubble separating mechanism and an auxiliary bubble separating mechanism, which has a guiding portion for changing the flow direction of introduced fluid and a different form from the centrifugal bubble separating mechanism, are provided. Therefore, in addition to minuscule bubbles it is also possible to separate large bubbles that could not be completely separated using the centrifugal bubble separating mechanism. Furthermore, even in cases where bubbles would remain because the centrifugal bubble separating mechanism alone is unable to separate a large amount of bubbles, the present invention can separate many bubbles with extremely high efficiency.

When the centrifugal bubble separating mechanism is provided upstream and the auxiliary bubble separating mechanism is provided downstream, small bubbles are efficiently separated upstream. Meanwhile, large bubbles or residual bubbles left from a large amount of bubbles which were not separated upstream are reliably and easily separated by the downstream separating mechanism. Therefore, all bubbles can be efficiently separated.

When the centrifugal bubble separating mechanism is provided downstream and the auxiliary bubble separating mechanism is provided upstream, the bubbles are ultimately separated in an efficient manner similar to the above, regardless of whether there are large bubbles or a large amount of bubbles.

If the guiding portion is a partition formed from a board-shaped body, then it is possible to achieve a simple structure, and further possible to efficiently separate bubbles from the fluid.

A longer separation distance and separation time are possible when the auxiliary bubble separating mechanism is a flow passage of the bent body provided with the gas discharging part on an upper wall face thereof. Therefore, bubble separation can be even more efficiently and reliably achieved in the auxiliary separating mechanism.

If the second fluid discharging part in the auxiliary bubble separating mechanism is an opening and closing valve that opens and closes depending on the pressure within the first bubble separator body, then bubbles can be more conveniently and efficiently separated from the fluid.

DESCRIPTION OF REFERENCE NUMERALS AND SIGNS 1, 2, 3, 4, 5, 7, 57: bubble separator,
10, 30, 50, 70: centrifugal bubble separating mechanism,
11, 31, 51, 71: first bubble separator body, 12, 32, 52, 72: first fluid introducing part, 13, 33, 53, 73: first fluid discharging part, 14, 34, 54, 74: first gas discharging part,
20, 40, 60, 80: auxiliary bubble separating mechanism, 21, 41, 61, 81, 85: second bubble separator body, 22, 42, 62, 82: second fluid introducing part, 23, 43, 63, 83: second fluid discharging part, 24, 44, 64, 84: second gas discharging part,
9, 49, 97: oil tank, and 91, 92, 93, 94, 95: guiding portion.

DETAILED DESCRIPTION OF THE PREFERRED EMBODIMENTS

A detailed description of a bubble separator according to the present invention follows below.

The bubble separator according to the present invention is intended to remove air bubbles contained in a fluid, and is provided with a centrifugal bubble separating mechanism and further provided with an auxiliary bubble separating mechanism downstream or upstream of the centrifugal bubble separating mechanism.

1. Centrifugal Bubble Separating Mechanism

The centrifugal bubble separating mechanism is provided with a first bubble separator body, a first fluid introducing part, a first fluid discharging part, and a first gas discharging part.

The above-mentioned "first bubble separator body" is not particularly limited in terms of shape, size, material and the like, formed in a generally cylindrical shape. For example, the body may have a cylindrical tapered portion on a lower side.

The above-mentioned "first fluid introducing part" is provided on the first bubble separator body and introduces fluid mixed with bubbles inside the first bubble separator body in the tangential direction; however, the shape, size, material and the like thereof are not particularly limited.

For example, the first fluid introducing part may be a pipe that extends from an upper peripheral wall in the tangential direction of the body. Accordingly, the introduction of fluid enables swirling of the fluid within the body. The fluid introducing part may also, for example, be in communication with a scavenge pump that intakes oil from the engine and sends such oil into the fluid introducing part.

A swirling mechanism that swirls the introduced fluid is not particularly limited in terms of its configuration, swirl mode and the like, provided that the swirling mechanism swirls the fluid that flows in the first bubble separator body around in the axial direction of the first bubble separator body. A swirling mechanism that takes advantage of the rotating force generated by the inflow of fluid may be used, for example. Also, a swirling mechanism may be installed that has a rotatably supported rotator whose rotation axis center is centered on the cyclone separation chamber (separator body) and a driving source that rotates the rotator. It is further possible to combine the above two methods with other methods.

The centrifugal bubble separating mechanism separates bubbles using a swirling mechanism in the cyclone separation chamber, and thus excels at removing minuscule bubbles (normally bubbles with a diameter of roughly up to 3 mm, or approximately 1 to 3 mm). If the swirling mechanism takes advantage of the rotating force generated by the inflow of fluid, bubbles can be even more easily and efficiently separated from the fluid.

Figure 1:
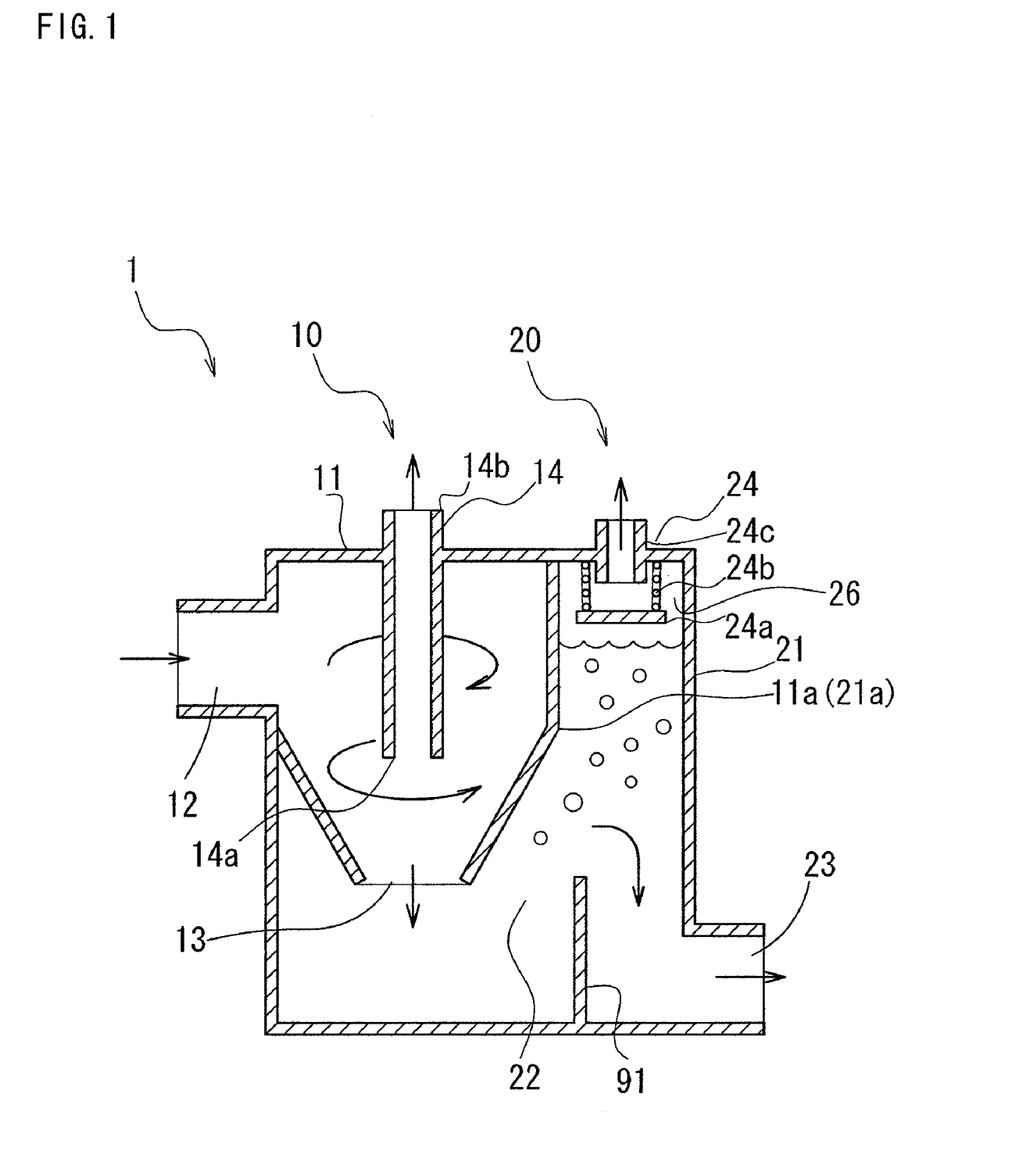
FIG. 1 is a schematic cross-sectional view of a bubble separator according to a first embodiment.

The above-mentioned "first fluid discharging part" is provided in the first bubble separator body and discharges fluid separated by swirling. The first fluid discharging part is not particularly limited in terms of its position, configuration, shape and the like, provided that the first fluid discharging part is capable of discharging fluid after bubbles have been separated from such fluid by the swirling mechanism. As shown in FIG. 1 for example, a first fluid discharging part 13 may be disposed at the lower portion of the cyclone separation chamber.

Figure 2:
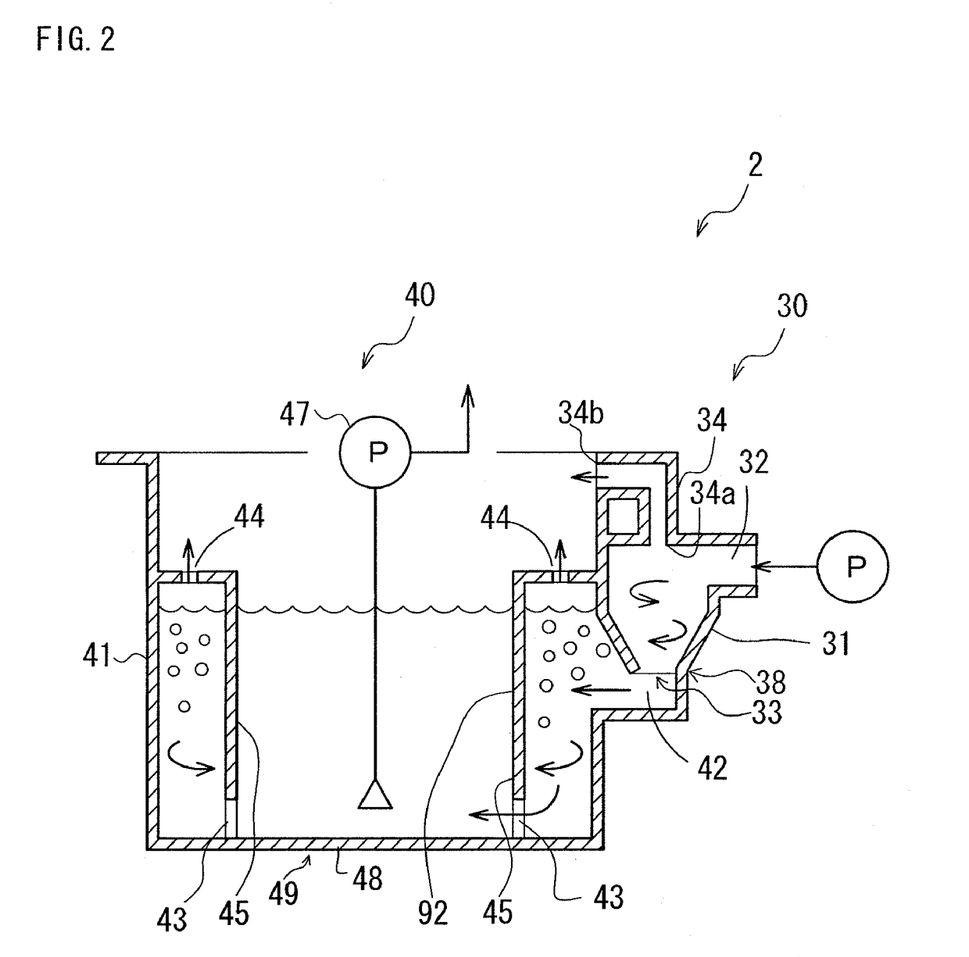
FIG. 2 is a schematic cross-sectional view of a bubble separator according to a second embodiment.

The above-mentioned "first gas discharging part" is provided in the first bubble separator body and discharges gas separated by swirling. The first gas discharging part is not particularly limited in terms of its position, configuration, shape and the like, provided that the first gas discharging part can discharge separated bubbles to outside the body. As shown in FIG. 1 for example, a first gas discharging part 14 may be a cylindrical and tubular body that extends downward from the upper portion of the cyclone separation chamber, or as shown in FIG. 2, simply a hole 34a that is not provided with a tubular body.

2. Auxiliary Bubble Separating Mechanism

Figure 3:
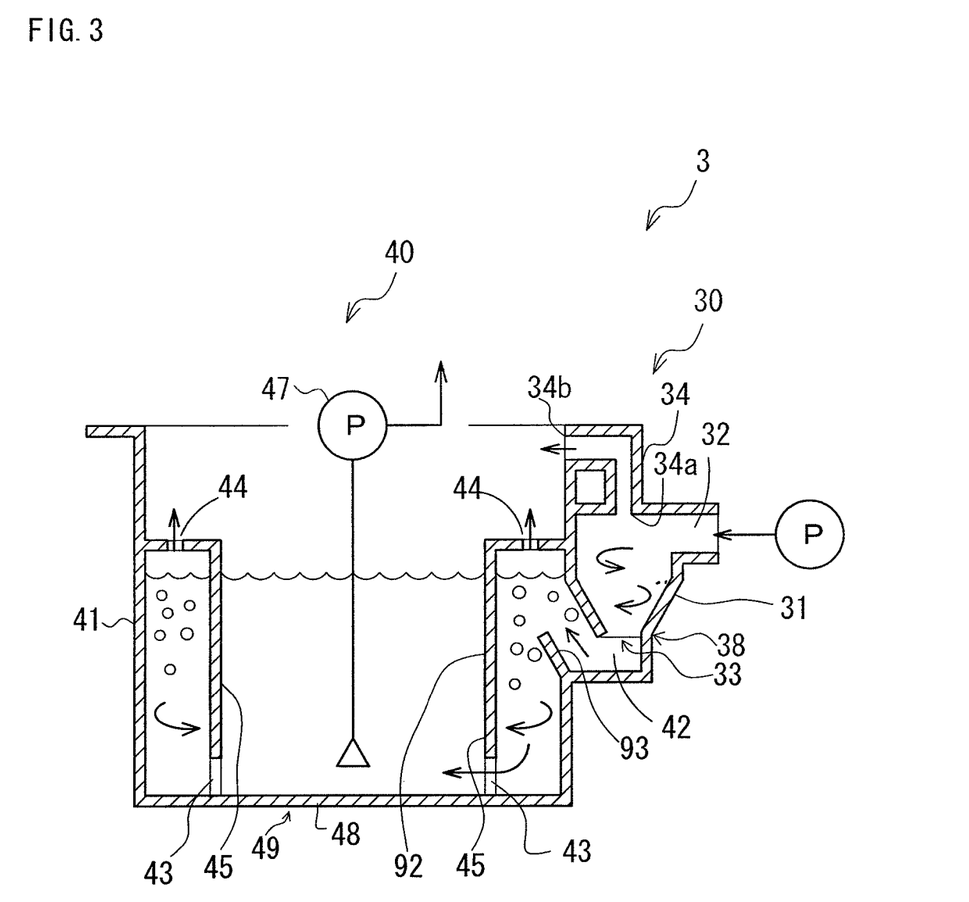
FIG. 3 is a schematic cross-sectional view of a bubble separator according to a third embodiment.
Figure 4:
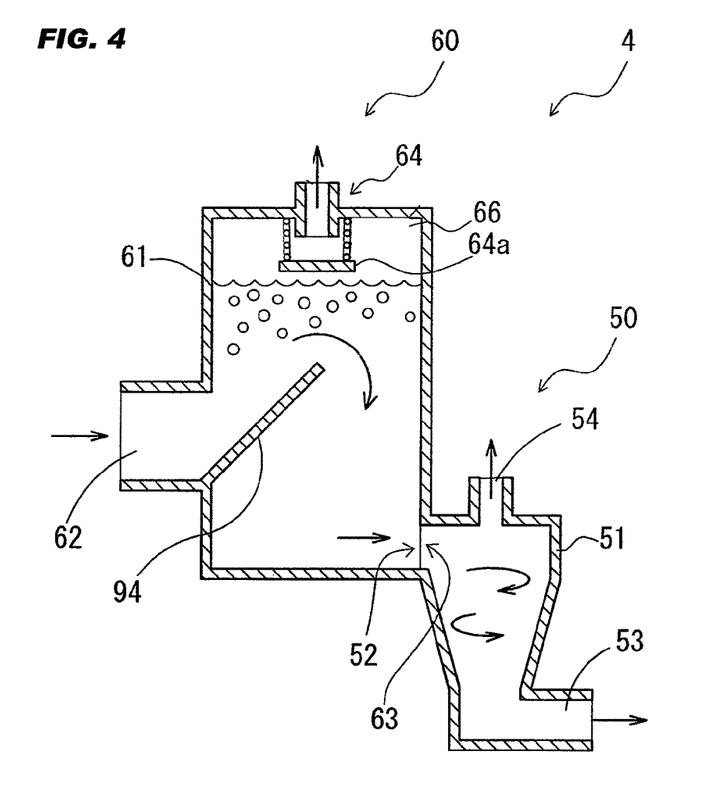
FIG. 4 is a schematic cross-sectional view of a bubble separator according to a fourth embodiment.
Figure 5:
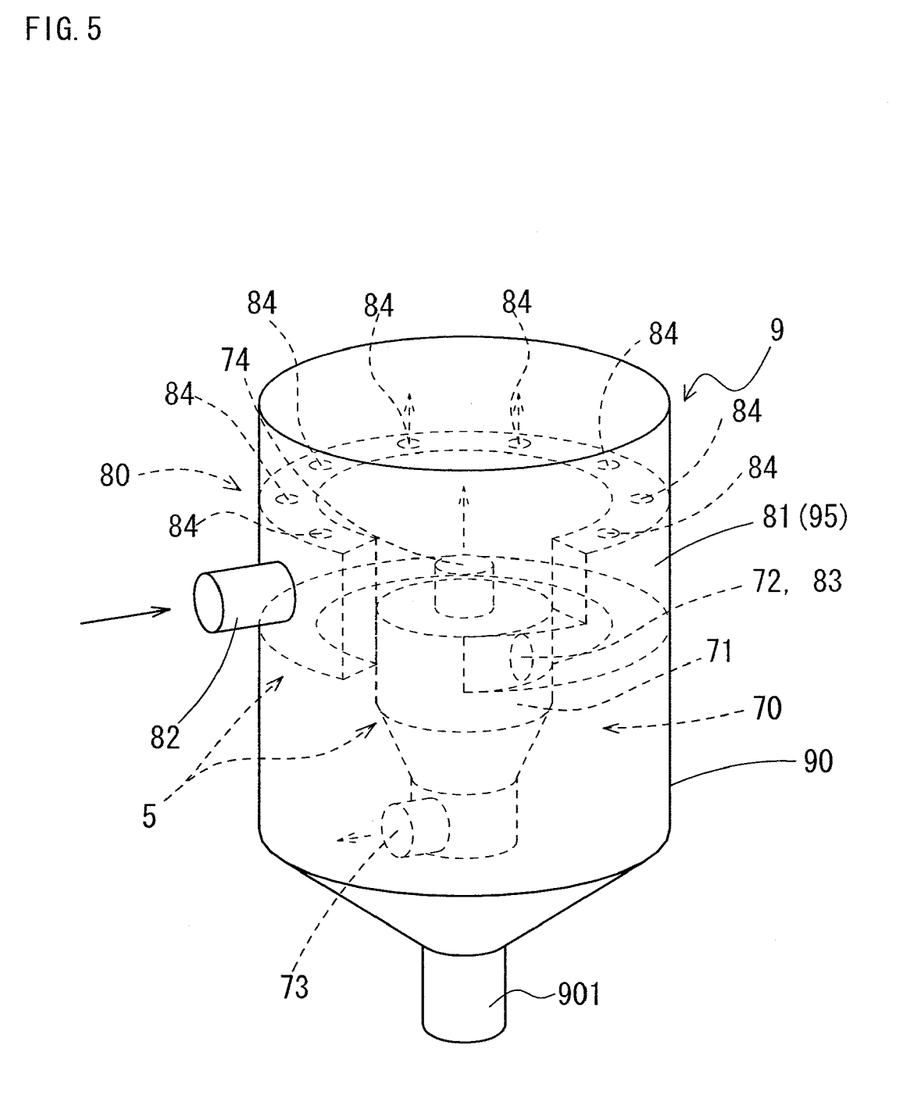
FIG. 5 is a schematic perspective view of an oil tank according to a fifth embodiment.
Figure 6:
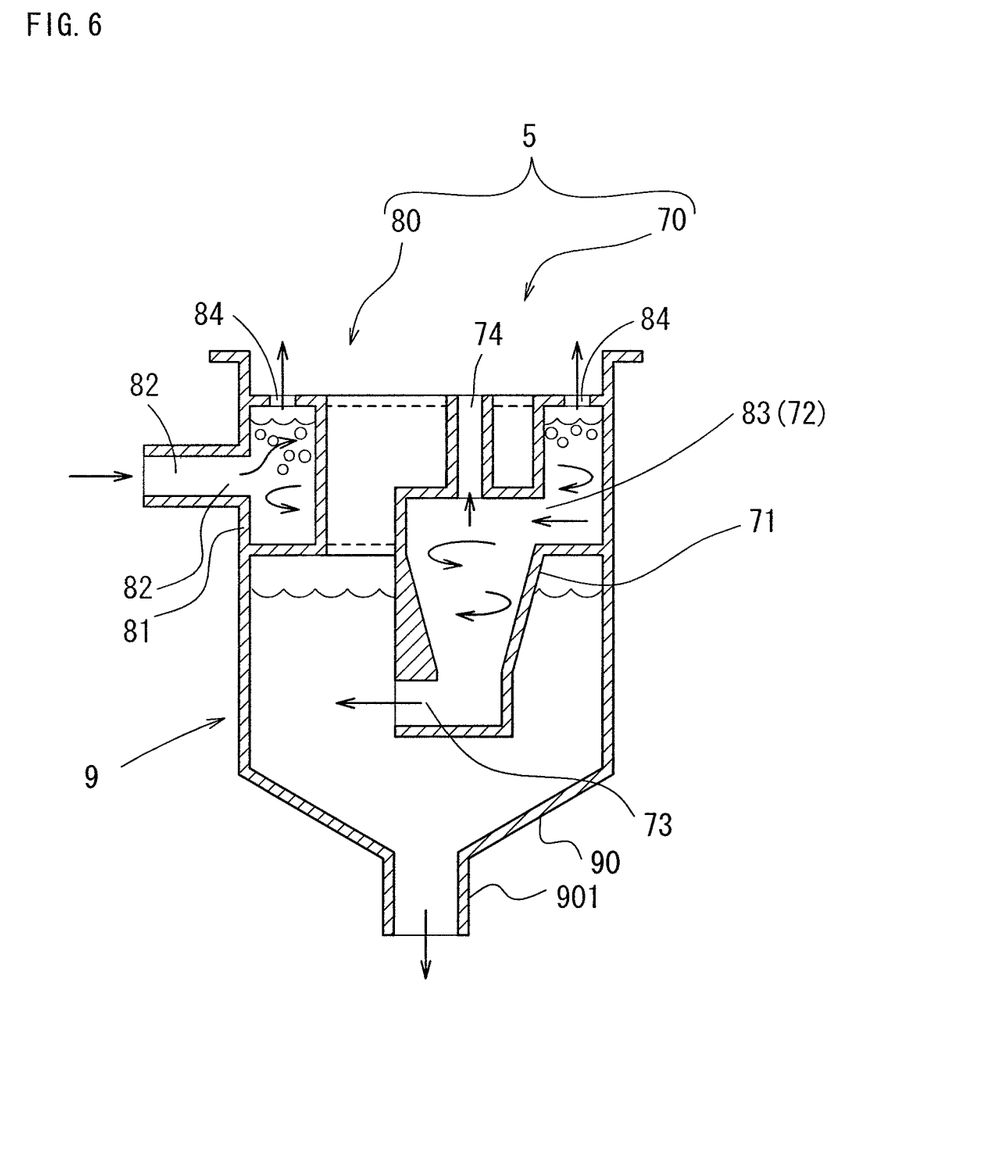
FIG. 6 is a schematic cross-sectional view of another oil tank according to the fifth embodiment.

The auxiliary bubble separating mechanism is further provided downstream or upstream of the centrifugal bubble separating mechanism. Examples of the auxiliary bubble separating mechanism arranged downstream are shown in FIGS. 1 to 3, while examples of the auxiliary bubble separating mechanism arranged upstream are shown in FIGS. 4 to 6. Moreover, if sufficient bubble separation cannot be achieved by the above, then either of these separating mechanisms may also be further arranged downstream or upstream thereof.

The above-mentioned "auxiliary bubble separating mechanism" is provided with a second bubble separator body, a second fluid introducing part, a second fluid discharging part, and a second gas discharging part. The auxiliary bubble separating mechanism is well suited for removing large bubbles whose removal may be difficult to achieve using the centrifugal bubble separating mechanism. In cases where there are too many bubbles and the centrifugal bubble separating mechanism cannot sufficiently remove the bubbles, combining the auxiliary bubble separating mechanism is possible to efficiently remove the bubbles in the fluid.

The above-mentioned "second bubble separator body" has a guiding portion for changing the flow direction of introduced fluid, and is provided adjacent to the first bubble separator body. The second bubble separator body is not particularly limited, provided that the guiding portion is provided for changing the flow direction of introduced fluid and has an overall shape enabling bubble separation. Furthermore, the second bubble separator body is not particularly limited in terms of its size, material and the like, provided that bubble separation can be achieved.

For example, a portion (e.g., 21a in FIG. 1) of the second bubble separator body may also be used as a portion (e.g., 11a in FIG. 1) of the first bubble separator body. In addition, the second bubble separator body may be separate from the first bubble separator body and the second fluid discharging part in communication with the first fluid introducing part (see FIG. 4 or the like).

The shape of the second bubble separator body may be a generally cylindrical shape (such as a circular cylindrical shape or a square cylindrical shape) or other shape (see FIGS. 1 to 4). Other conceivable shapes for the second bubble separator body include an overall circular bent body whose upper surface is provided with a discharge hole for discharging separated bubbles (see FIG. 7), and a circular bent body with a notched portion (see FIG. 5). A quadrangular shape (such as a rectangle, square or other shape) is normally used for the vertical cross-sectional shape of such a bent body with a bent flow passage (see FIGS. 5 and 7).

The above-mentioned "guiding portion" is intended to change the flow direction of fluid that is introduced to the separation chamber from the second fluid introducing part, which is provided in the auxiliary bubble separating mechanism. The guiding portion is not particularly limited in terms of its shape, size or the like, provided that the guiding portion can achieve its intended function.

For example, the guiding portion may be a partition formed from a board-shaped body (see guiding portions 91, 93 and 94 shown in FIGS. 1, 3 and 4). Or as described above, the guiding portion may be an overall circular bent body (see FIG. 7) or a circular bent body with a notched portion (see FIG. 5). If the guiding portion is a board-shaped body, a suitable inclined angle with respect to a supporting body thereof may be arbitrarily selected; however, the inclined angle is normally near 90 degrees (approximately 80 to 100 degrees or the like, see FIGS. 1 and 2), or near 45 degrees (approximately 40 to 50 degrees or the like, see FIGS. 3 and 4).

Conceivable guiding portions having a board-shaped body include the following:

(1) a board-shaped body 91, which changes the flow of introduced fluid upward when such fluid impacts the board-shaped body (in this case, a long flow path can be secured if the upward flow further impacts a separator body thereforward and is changed downward) as shown in FIG. 1;

(2) a board-shaped body 92, which is a partition of a bubble separator body 41 for changing the flow of introduced fluid downward when such fluid impacts the board-shaped body as shown in FIG. 2;

(3) a board-shaped body 93, which changes the flow of introduced fluid upward when such fluid impacts the board-shaped body (in this case, a long flow path can be secured if the upward flow further impacts a separator body thereforward and is changed downward) as shown in FIG. 3; and (4) a board-shaped body 94, which changes the flow of introduced fluid upward (in this case, a long flow path can be secured if the upward flow further impacts a separator body thereforward and is changed downward) as shown in FIG. 4.

Figure 7:
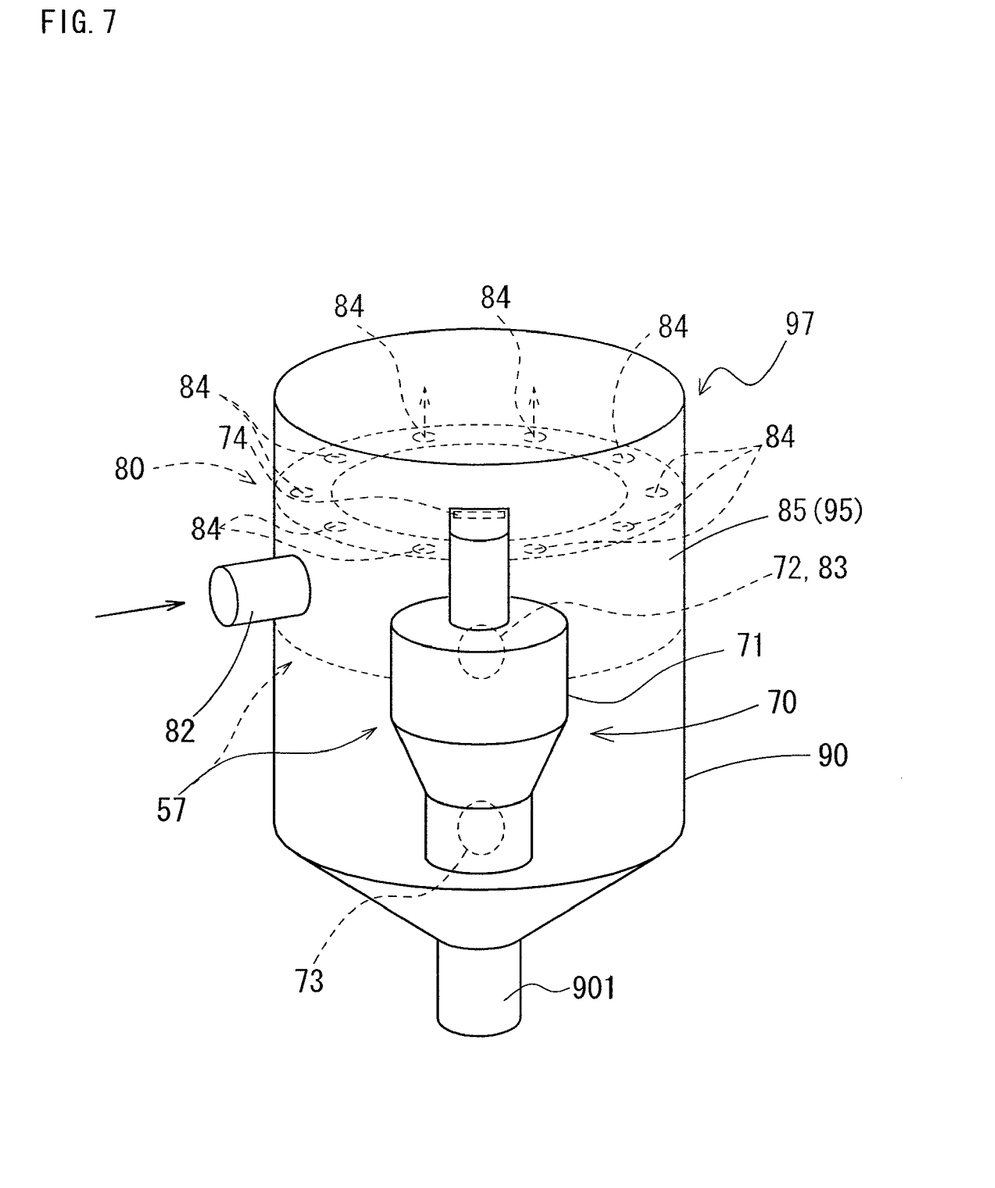
FIG. 7 is a schematic perspective view of an oil tank according to a sixth embodiment.

Furthermore, as shown in FIGS. 5 and 7, the guiding portion may also be a bent body 95, which changes the flow of introduced fluid to the horizontal direction (in this case, in addition to serving as the guiding portion, the bent body 95 at the same time also structures the second bubble separator body). In such case, the fluid can flow through a long curved flow path, which thus secures sufficient separation time for excellent separation efficiency.

The above-mentioned "second fluid introducing part" is provided in the second bubble separator body, and introduces fluid that requires bubble separation. The second fluid introducing part is not particularly limited in terms of its shape, size, material or the like. In addition, the second fluid introducing part may be formed between the guiding portion 91 and a body (11a and 21a) that is shared by the first bubble separator body and the second bubble separator body (see FIG. 1). Alternatively, the second fluid introducing part may also be formed between the guiding portion 94, which is a board-shaped body that protrudes at an angle, and the second bubble separator body (see FIG. 4).

The above-mentioned "second fluid discharging part" is not particularly limited in terms of its shape, size, material, position or the like, provided that the second fluid discharging part is provided in the second bubble separator body and discharges separated fluid. For example, as shown in FIGS. 1 to 4, the second fluid discharging part may be formed as a lower bottom wall of the body, or as shown in FIG. 2, the second fluid discharging part may also have a structure pulled by a pumping mechanism.

The above-mentioned "second gas discharging part" is not particularly limited in terms of its shape, size, material or the like, provided that the second gas discharging part is provided in the above body and discharges separated bubbles to outside the body.

In addition, the mechanism for discharging the bubbles may be a spring valve or an electromagnetic valve that opens and closes depending on the pressure within the first bubble separator body. For example, as shown in FIG. 1, a second gas discharging part 24 can be structured from a spring type discharge valve 24a, a spring 24b, and a discharge pipe 24c. In other words, when the pressure decreases in a cavity portion 26, which is a bubble separation chamber, the spring type discharge valve 24a opens and bubbles (gas) are discharged to outside the body through the discharge pipe 24c.

The average grain diameter of the bubbles separated and discharged by the centrifugal bubble separating mechanism is preferably smaller than the average grain diameter of the bubbles separated and discharged by the auxiliary bubble separating mechanism. This is because the auxiliary bubble separating mechanism is provided for the purpose of removing large bubbles that may be difficult for the centrifugal bubble separating mechanism to remove. Thus, providing the centrifugal bubble separating mechanism and the auxiliary bubble separating mechanism capable of discharging bubbles with different average grain diameters enables reliable and efficient separation of bubbles both large and small from the fluid.

Furthermore, the present bubble separator may have a flow control mechanism, which controls the fluid flow amount, provided on an end side of the bubble separator or between the centrifugal bubble separating mechanism and the auxiliary bubble separating mechanism. It is also possible to provide a flow control mechanism that controls the flow amount of fluid that is discharge to the first fluid discharging part or the second fluid discharging part.

Figure 9:
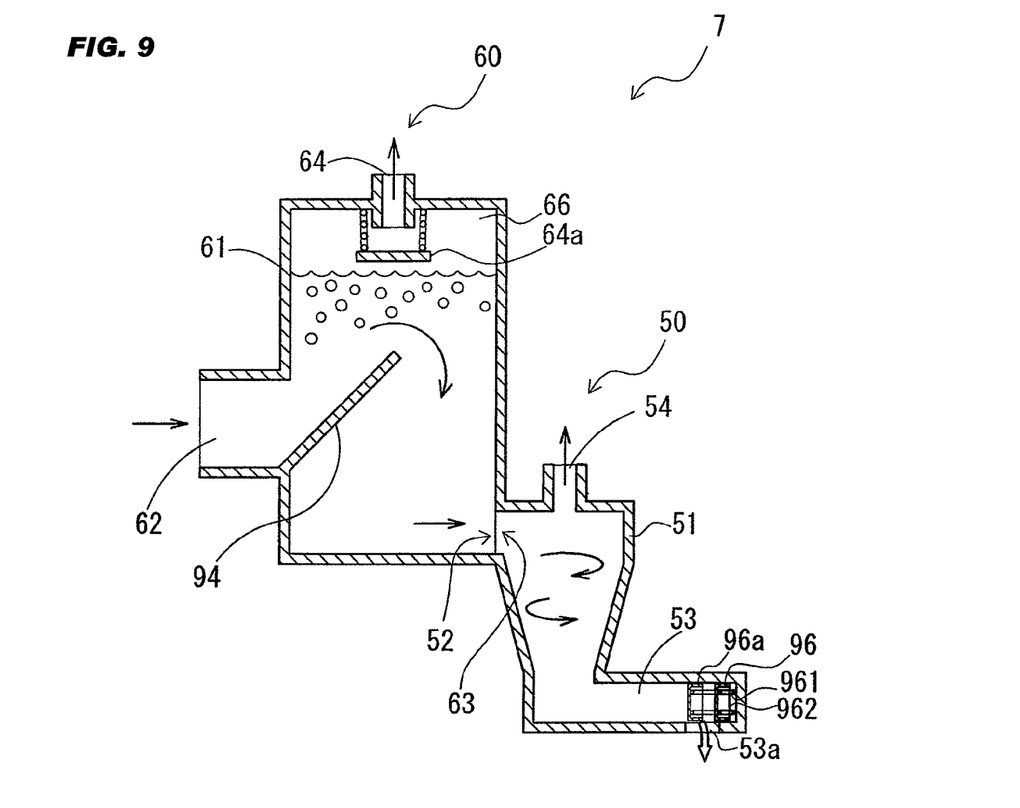
FIG. 9 is a schematic cross-sectional view of a bubble separator with a flow control mechanism.

Such a flow control mechanism is conceivably provided, for example, with a valve opened and closed by a spring or the like, provided that the flow control mechanism controls the fluid flow amount and is capable of maintaining the pressure constant in the centrifugal bubble separating mechanism or the auxiliary bubble separating mechanism before the flow control mechanism. An example includes a bubble separator 7 as shown in FIG. 9, where a flow control valve 96 is opened and closed by a spring and is provided immediately before a discharge hole 53a of a first fluid discharging part 53. The flow control valve 96 is formed from a valve body 961 and a spring 962. The valve body 961 is movably supported so as to be capable of changing an opening amount of the discharge hole 53a, and the spring 962 is a biased member that is biased in a direction that moves the valve body 961 so as to narrow the opening of the discharge hole 53a. If the pressure within a centrifugal bubble separating mechanism 50 is low, then the pressure is raised by moving the position of the flow control valve 96a to decrease the amount of flow discharged. Meanwhile, if the pressure within the centrifugal bubble separating mechanism 50 is high, then the pressure can be lowered by moving the position of the flow control valve 96 to increase the amount of flow discharged.

By maintaining the pressure within the centrifugal bubble separating mechanism 50 constant in such a manner, it is possible to keep bubbles from becoming growing or shrinking due to pressure variations. Also, it is possible for the bubbles to maintain a size that facilitates bubble removal by the bubble separating mechanisms 50 and 60 of the bubble separator 7, thereby achieving efficient bubble removal.

3. Oil Tank

An oil tank provided with the bubble separator according to the present invention may have a structure including, for example, the bubble separator with at least a portion of the bubble separator disposed within a tank chamber.

In such case, a fluid introducing part 32 of a bubble separator 3 is in communication with a scavenge pump that intakes oil from an oil pan of the engine and delivers the oil to the fluid introducing part, as shown in FIG. 3 for example. Furthermore, an oil discharging part provided in the lower portion of the oil tank is in communication with a feed pump that intakes oil from the oil tank and delivers the oil to the engine. Thus, it is possible to provide an oil tank structure well suited to a dry sump system as a mode for lubricating an engine.

Embodiments

The present invention will be described in detail below based on embodiments and in reference to the accompanying drawings.

Note that in the present embodiments, examples are given of a bubble separator according to the present invention which is used in a lubrication system of an automotive engine and separates bubbles from oil mixed with bubbles.

[1] First Embodiment (1) Structure of the Bubble Separator 1

As shown in FIG. 1, a bubble separator 1 according to the present invention has a centrifugal bubble separating mechanism 10 and an auxiliary bubble separating mechanism 20 provided downstream thereof.

The centrifugal bubble separating mechanism 10 has a first bubble separator body 11, and a first fluid introducing part 12 that introduces oil (oil containing bubbles) into a cyclone separation chamber inside the first bubble separator body 11 in the tangential direction.

Furthermore, a first fluid discharging part 13 that discharges oil separated by swirling (primary separated oil containing residual bubbles) is provided in the lower portion of the cyclone chamber. Also a first gas discharging part 14 that discharges bubbles (gas) separated by swirling is provided forming in a cylindrical and tubular body extending from the upper portion toward the lower portion of the cyclone chamber.

The auxiliary bubble separating mechanism 20 has a second bubble separator body 21, and a second fluid introducing part 22 that introduces oil (primary separated oil containing residual bubbles) to the second bubble separator body 21. The second fluid introducing part 22 is formed between a guiding portion 91 and a body 11a (21a), which are shared by the first bubble separator body and the second bubble separator body. The second bubble separator body 21 further includes a second fluid discharging part 23 that discharges separated oil at a lower bottom wall of the body.

In addition, a second gas discharging part 24 that discharges separated bubbles (gas) is provided at the upper portion of the body. The second gas discharging part 24, as shown in FIG. 1, is structured from a spring type discharge valve 24a, a spring 24b, and a discharge pipe 24c. When the pressure decreases within a bubble separation chamber, the spring type discharge valve 24a opens and bubbles (gas) are discharged to outside the body through the discharge pipe 24c.

Moreover, the second bubble separator body 21 is provided with a guiding portion 91, which is perpendicular to a bottom face and formed from a board-shaped body for changing the flow direction of introduced oil (primary separated oil containing residual bubbles).

(2) Operation of the Bubble Separator 1

In the bubble separator 1 according to the first embodiment, as shown in FIG. 1, oil (oil containing bubbles) is introduced to the first bubble separator body 11 from the first fluid introducing part 12. Accordingly, the centrifugal force of the introduced oil causes the oil with a large specific gravity to collect on an inner wall side of the first bubble separator body 11, while the bubbles with a small specific gravity collect on a center side of the first bubble separator body 11. As a consequence, the separated bubbles rise from an opening lower end 14a of the cylindrical-shaped first gas discharging part 14 toward an opening upper end 14b, and are discharged to outside the first bubble separator body 11.

Meanwhile, the primary separated oil containing residual bubbles is discharged from the first fluid discharging part 13 and flows toward the second fluid introducing part 22. The flow direction of the oil is then changed by the guiding portion 91 upward in the second bubble separator body 21. Accordingly, since the primary separated oil contains relatively large bubbles, the buoyancy of the bubbles causes the residual bubbles to collect in a cavity portion 26. An increase in bubbles results in a decrease of pressure in the cavity portion 26. The discharge valve 24a provided in the second gas discharging part 24 thus opens and the collected bubbles are discharged.

The discharge valve 24a is opened and closed by the spring 24b depending on the pressure within the cavity portion 26.

The oil separated from the bubbles is discharged to outside the bubble separator 1 through the second fluid discharging part 23.

The bubble separator 1 of the present embodiment can be disposed within the oil tank of a dry sump lubrication system, and can also be disposed in an oil passage (pipe or the like) downstream of an oil pump in a wet sump lubrication system.

(3) Effects of the First Embodiment

In the present embodiment, a two-stage bubble separating mechanism including a first bubble separating mechanism and a second bubble separating mechanism is used. Therefore, bubble separation that could not be achieved in one of the stages is achieved in the other. Thus, bubble separation can be reliably performed even when there is a large amount of bubbles.

Furthermore, in the present embodiment, the first bubble separating mechanism is realized by generating a swirling force in the oil due to its introduction from the oil pump, and the second bubble separating mechanism is realized by utilizing the buoyancy of the bubbles in oil already subjected to primary bubble separation. There is thus no need to provide a special driving source, and a more simple and inexpensive structure can be achieved.

[2] Second Embodiment (1) Structure of the Bubble Separator 2

As shown in FIG. 2, a bubble separator 2 according to the present invention has a centrifugal bubble separating mechanism 30 and an auxiliary bubble separating mechanism 40 provided downstream thereof, similar to the first embodiment.

The centrifugal bubble separating mechanism 30 has a first bubble separator body 31, a first fluid introducing part 32 that introduces oil (oil containing bubbles) inside the first bubble separator body 31 in the tangential direction, a first fluid discharging part 33 that discharges oil separated by swirling (primary separated oil containing residual bubbles), and a first gas discharging part 34 that discharges bubbles (gas) separated by swirling.

The auxiliary bubble separating mechanism 40 has a second bubble separator body 41, a second fluid introducing part 42 that introduces oil (primary separated oil containing residual bubbles) to the second bubble separator body 41, a second fluid discharging part 43 that discharges separated oil, and a second gas discharging part 44 that discharges separated bubbles (gas). The second bubble separator body 41 further includes a guiding portion 92 formed from a board-shaped body for changing the flow direction of introduced oil.

Unlike the first embodiment, the first gas discharging part 34 does not have the tubular body of the first gas discharging part 14 shown in FIG. 1, which extends downward from the upper portion of the first bubble separator body 11. As shown in FIG. 2, the first gas discharging part 34 is a hole 34a of an opening lower end that is connected to an opening upper end 34b. However, the same effect as the first gas discharging part 14 of the first embodiment is achieved.

(2) Operation of the Bubble Separator 2

As shown in FIG. 2, the role of the guiding portion 92 in the second embodiment is fulfilled by an inner wall 45 face of the second bubble separator body. Also, disposing a bottom portion 38 of the first bubble separator 31 farther upward than a bottom portion 48 of the second bubble separator body 41 has the subsequent advantage of ensuring that oil discharged from the first fluid discharging part 33 and introduced to the second fluid introducing part 42 is already in the upper portion of the second bubble separator body 41.

Oil discharged to an oil tank 49 from the second fluid discharging part 43 is drawn from the bubble separator 2 by a pump 47.

(3) Effects of the Second Embodiment

The present embodiment adopts a structure generally similar to the first embodiment. Therefore, effects generally similar to the first embodiment can be obtained.

[3] Third Embodiment

As shown in FIG. 3, a bubble separator 3 according to a third embodiment further includes a guiding portion 93 in the bubble separator 2 of the second embodiment. Thus, the flow of oil discharged from the first fluid discharging part 33 and introduced to the second fluid introducing part 42 is further promoted toward the upper portion of the second bubble separator body 41 by the guiding portion 93.

Other structures, operations and effects are similar to the bubble separator 2 of the second embodiment and descriptions therefor are thus omitted.

[4] Fourth Embodiment (1) Structure of the Bubble Separator 4

As shown in FIG. 4, a bubble separator 4 according to a fourth embodiment has an auxiliary bubble separating mechanism 60 and a centrifugal bubble separating mechanism 50 provided downstream thereof.

The auxiliary bubble separating mechanism 60, as FIG. 4 shows, has a second bubble separator body 61, a second fluid introducing part 62 that introduces oil (oil containing bubbles) to the second bubble separator body 61, a second fluid discharging part 63 that discharges separated oil (primary separated oil containing residual bubbles), and a second gas discharging part 64 that discharges primary separated bubbles (gas). The second bubble separator body 61 further includes a guiding portion 94 formed from a board-shaped body for changing the flow direction of introduced oil, which is provided at an inclined angle of 45 degrees.

In addition, the centrifugal bubble separating mechanism 50 has a first bubble separator body 51, a first fluid introducing part 52 that introduces oil (primary separated oil containing residual bubbles) inside of the first bubble separator body 51 in the tangential direction, a first fluid discharging part 53 that discharges oil separated by swirling, and a first gas discharging part 54 that discharges bubbles (gas) separated by swirling.

(2) Operation of the Bubble Separator 4

In the bubble separator 4 according to the fourth embodiment, as shown in FIG. 4, oil (oil containing bubbles) is introduced to the second bubble separator body 61 from the second fluid introducing part 62. The flow direction of the oil is then changed by the guiding portion 94 upward in the second bubble separator body 61. Accordingly, relatively large-sized bubbles contained in the oil flowing into the upper portion of the second bubble separator body 61 collect toward a cavity portion 66 due to their considerable buoyancy. An increase in bubbles results in a decrease of pressure in the cavity portion 66. A discharge valve 64*a* provided in the second gas discharging part 64 thus opens and the collected bubbles are discharged.

Relatively large-sized bubbles are thus removed from oil discharged from the second fluid discharging part 63 due to the primary separation. Therefore, oil introduced to the first bubble separator body 51 includes relatively minuscule bubbles.

The centrifugal force of oil introduced to the first bubble separator body 51 from the first fluid introducing part 52 causes the oil with a large specific gravity to collect on an inner wall side of the first bubble separator body 51, while the bubbles with a small specific gravity collect on a center side of the first bubble separator body 51. As a consequence, the separated bubbles are discharged from the cylindrical-shaped first gas discharging part 54 to outside the first bubble separator body 51.

Secondary separated oil is discharged from the first fluid discharging part 53.

(3) Effects of the Fourth Embodiment

The fourth embodiment also combines a first bubble separating mechanism and a second bubble separating mechanism, similar to the first to third embodiments, and has identical points of use. Therefore, bubble separation effects generally similar to the first to third embodiments can be obtained.

[5] Fifth Embodiment (1) Structure of the Bubble Separator 5 and the Oil Tank 9

As shown in FIGS. 5 and 6, an oil tank 9 according to a fifth embodiment is a container 90 provided with a discharge passage 901 therebelow, and a bubble separator 5 therein. The bubble separator 5 has an auxiliary bubble separating mechanism 80 and a centrifugal bubble separating mechanism 70 provided downstream thereof.

The auxiliary bubble separating mechanism 80, as FIGS. 5 and 6 shows, has a second bubble separator body 81, a second fluid introducing part 82 that introduces oil (oil containing bubbles) to the second bubble separator body 81, a second fluid discharging part 83 that discharges separated oil (primary separated oil containing residual bubbles), and second gas discharging parts 84 that discharge primary separated bubbles (gas).

The multiple (8 parts, in FIG. 5) second gas discharging parts 84 are arranged along the circumferential direction of the upper portion of the second bubble separator body 81 at roughly equal intervals, as shown in FIG. 5. Note, however, that the interval may be progressively widened or narrowed.

The second bubble separator body 81 forms a circular bent body with a notched portion, as shown in FIG. 5. The bent body has a flow passage with this generally circular shape, and the vertical cross section of the bent body is a rectangular shape.

In other words, the guiding portion 95 is also the bent body, which changes the flow of introduced fluid (oil containing bubbles) to the horizontal direction (in this case, in addition to serving as the guiding portion, the bent body at the same time also structures the second bubble separator body 81). In such case, the fluid (oil containing bubbles) can flow through a long generally circular flow path, which thus secures sufficient separation time for excellent separation efficiency.

In addition, the centrifugal bubble separating mechanism 70 has a first bubble separator body 71, a first fluid introducing part 72 that introduces oil (primary separated oil containing residual bubbles) inside the first bubble separator body 71 in the tangential direction, a first fluid discharging part 73 that discharges oil separated by swirling, and a first gas discharging part 74 that discharges bubbles (gas) separated by swirling.

(2) Operation of the Bubble Separator 5 and the Oil Tank 9

Oil introduced from the second fluid introducing part 82 is subjected to bubble separation by the auxiliary bubble separating mechanism 80 of the bubble separator 5 and the centrifugal bubble separating mechanism 70 downstream of the auxiliary bubble separating mechanism 80. Thereafter, the oil is discharged from the first fluid discharging part 73 to the cylindrical-shaped (and partially tapered) container 90. The oil is subsequently led toward a lubrication channel from the discharge passage 901 provided in the container 90.

(3) Effects of the Fifth Embodiment

The oil discharge passage 901 provided in the lower portion of the oil tank 9 is in communication with a feed pump FP that intakes oil from the oil tank and delivers the oil to the engine. Thus, it is possible to provide an oil tank structure well suited to a dry sump system as a mode for lubricating an engine.

[6] Sixth Embodiment

Figure 8:
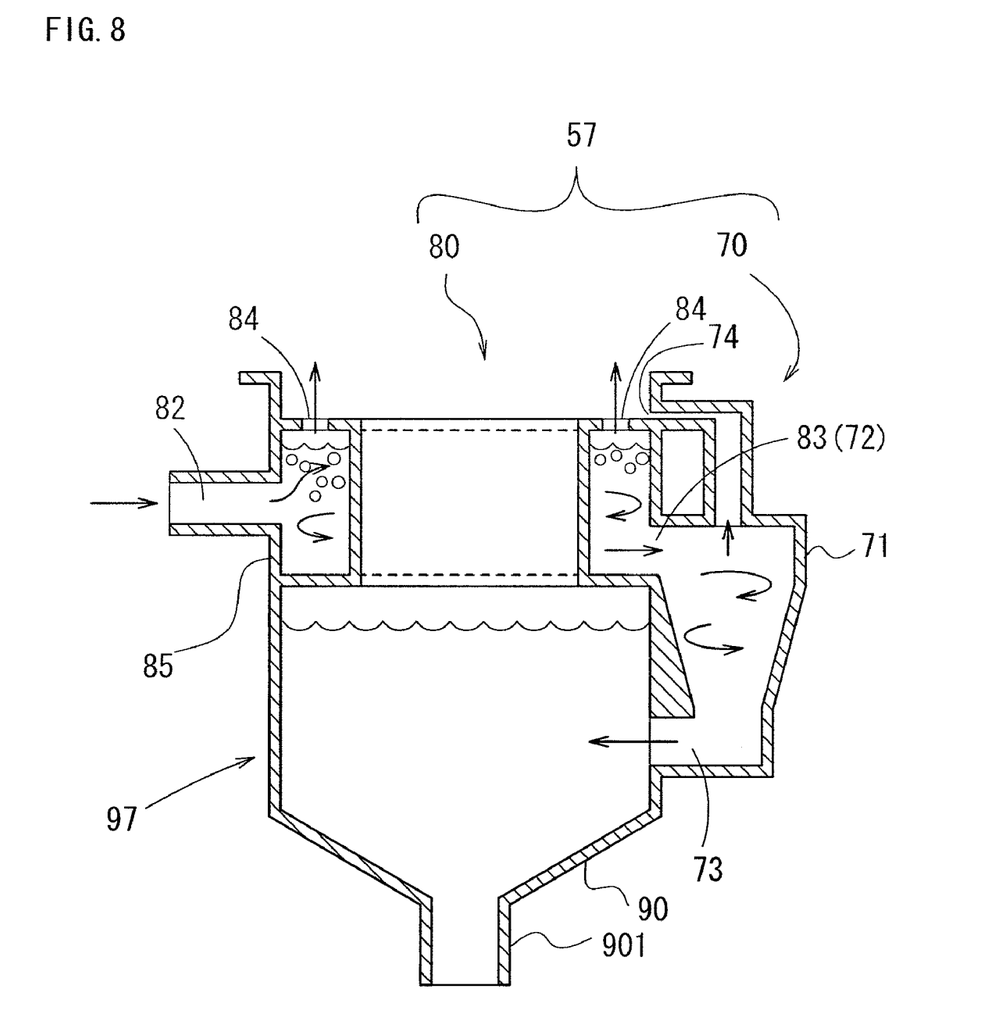
FIG. 8 is a schematic cross-sectional view of another oil tank according to the sixth embodiment.

A bubble separator 57 and an oil tank 97 according to a sixth embodiment have structures generally similar to the bubble separator 5 and the oil tank 9 according to the fifth embodiment. However, as FIGS. 7 and 8 show, the centrifugal bubble separating mechanism 70 is provided on the outer periphery (outside) of the oil tank 97. Also, while the shape of the second bubble separator body 81 of the bubble separator 5 is a bent body with a notched portion, the shape of a second bubble separator body 85 of the bubble separator 57 is a bent body with an overall circular shape. Other structures, operations and effects are generally similar to the fifth embodiment and descriptions therefor are thus omitted.

The bubble separator according to the present invention can be widely used as art that separates bubbles from a fluid mixed with bubbles. The bubble separator is particularly well suited as art that separates bubbles from oil used in a lubrication system for an engine and mixed with bubbles.

What is claimed is:

1. A bubble separator for removing bubbles included in a fluid, comprising:
   a centrifugal bubble separating mechanism; and
   an auxiliary bubble separating mechanism further provided on one of a downstream side and an upstream side of said centrifugal bubble separating mechanism, wherein
   said centrifugal bubble separating mechanism includes
      a first bubble separator body;
      a first fluid introducing part that is provided in said first bubble separator body, and introduces fluid mixed with bubbles inside said first bubble separator body in the tangential direction;
      a first fluid discharging part that is provided in said first bubble separator body, and discharges fluid separated by swirling; and
      a first gas discharging part that is provided in said first bubble separator body, and discharges bubbles separated by swirling, and
   said auxiliary bubble separating mechanism includes
      a second bubble separator body that is provided adjacent to said first bubble separator body, and has a guiding portion for changing the flow direction of introduced fluid;
      a second fluid introducing part that is provided in said second bubble separator body, and introduces said fluid;
      a second fluid discharging part that is provided in said second bubble separator body, and discharges separated fluid; and
      a second gas discharging part that is provided in said second bubble separator body, and discharges separated bubbles.

2. The bubble separator according to claim 1, wherein
said auxiliary bubble separating mechanism is provided on a downstream side of said centrifugal bubble separating mechanism,
said second bubble separator body has a guiding portion for changing a flow direction of said fluid that was subjected to primary separation and discharged from said first fluid discharging part of said centrifugal bubble separating mechanism while still including residual bubbles, and
said second fluid introducing part introduces said fluid that was subjected to primary separation.

3. The bubble separator according to claim 1, wherein
said auxiliary bubble separating mechanism is provided on an upstream side of said centrifugal bubble separating mechanism, and
said fluid that was subjected to primary separation by said auxiliary bubble separating mechanism and discharged from said second fluid discharging part is introduced to said first fluid introducing part.

4. The bubble separator according to claim 1, wherein
said guiding portion is a partition formed from a board-shaped body.

5. The bubble separator according to claim 1, wherein
said second gas discharging part in said auxiliary bubble separating mechanism has an opening and closing valve that opens and closes depending on a pressure within said first second bubble separator body.

6. The bubble separator according to claim 2, wherein
said guiding portion is a partition formed from a board-shaped body.

7. The bubble separator according to claim 2, wherein
said second gas discharging part in said auxiliary bubble separating mechanism has an opening and closing valve that opens and closes depending on a pressure within said second bubble separator body.

8. The bubble separator according to claim 3, wherein
said guiding portion is a partition formed from a board-shaped body.

9. The bubble separator according to claim 3, wherein
said auxiliary bubble separating mechanism is a bent body provided with said second gas discharging part on an upper wall face thereof.

10. The bubble separator according to claim 3, wherein
said second gas discharging part in said auxiliary bubble separating mechanism has an opening and closing valve that opens and closes depending on a pressure within said second bubble separator body.

11. The bubble separator according to claim 3, wherein
said first fluid discharging part in said centrifugal bubble separating mechanism has a flow control valve that controls said flow discharged from said first fluid discharging part.

12. The bubble separator according to claim 4, wherein
said second gas discharging part in said auxiliary bubble separating mechanism has an opening and closing valve that opens and closes depending on a pressure within said second bubble separator body.

13. The bubble separator according to claim 6, wherein
said second gas discharging part in said auxiliary bubble separating mechanism has an opening and closing valve that opens and closes depending on a pressure within said second bubble separator body.

14. The bubble separator according to claim 8, wherein
said second gas discharging part in said auxiliary bubble separating mechanism has an opening and closing valve that opens and closes depending on a pressure within said second bubble separator body.

15. The bubble separator according to claim 8, wherein
said first fluid discharging part in said centrifugal bubble separating mechanism has a flow control valve that controls said flow discharged from said first fluid discharging part.

16. The bubble separator according to claim 10, wherein
said first fluid discharging part in said centrifugal bubble separating mechanism has a flow control valve that controls said flow discharged from said first fluid discharging part.

* * * * *

UNITED STATES PATENT AND TRADEMARK OFFICE
CERTIFICATE OF CORRECTION

| | | |
|---|---|---|
| PATENT NO. | : 7,871,461 B2 | Page 1 of 1 |
| APPLICATION NO. | : 11/962502 | |
| DATED | : January 18, 2011 | |
| INVENTOR(S) | : Y. Saito | |

It is certified that error appears in the above-identified patent and that said Letters Patent is hereby corrected as shown below:

At column 14, line 16 (claim 5, line 5) of the printed patent, please delete the term "first" that appears before the term "second".

Signed and Sealed this
Twenty-third Day of August, 2011

David J. Kappos
*Director of the United States Patent and Trademark Office*